United States Patent
Mah

(10) Patent No.: US 11,051,541 B2
(45) Date of Patent: Jul. 6, 2021

(54) CLARIGEST COMPOSITION

(71) Applicant: DuraScience Inc., New York, NY (US)

(72) Inventor: James Nitit Mah, New York, NY (US)

(73) Assignee: Durascience, Inc., New York, NY (US)

( * ) Notice: Subject to any disclaimer, the term of this patent is extended or adjusted under 35 U.S.C. 154(b) by 19 days.

(21) Appl. No.: 16/679,277

(22) Filed: Nov. 10, 2019

(65) Prior Publication Data

US 2020/0068934 A1    Mar. 5, 2020

(51) Int. Cl.
```
A61K 36/00      (2006.01)
A23L 33/105     (2016.01)
A61K 36/54      (2006.01)
A61K 36/81      (2006.01)
A61K 36/48      (2006.01)
```

(52) U.S. Cl.
CPC ............ *A23L 33/105* (2016.08); *A61K 36/48* (2013.01); *A61K 36/54* (2013.01); *A61K 36/81* (2013.01)

(58) Field of Classification Search
CPC ....................................................... A61K 36/00
USPC ............................................................ 424/725
See application file for complete search history.

(56) References Cited

U.S. PATENT DOCUMENTS

2010/0202980 A1*  8/2010  Fogel .................. A61K 36/185
                                                                424/48

* cited by examiner

*Primary Examiner* — Michael V Meller

(57) ABSTRACT

A nutritional supplement composition is provided including an extract derived from common white kidney beans (*Phaseolus vulgaris*), Capsicum extract of the fruit of the *Capsicum frutescens* strain and Cinnamon extract of the bark of the *Cinnamonium cassia* strain. The nutritional supplement is in the form of a compound known as CLARIGEST™.

2 Claims, No Drawings

CLARIGEST COMPOSITION

BACKGROUND

In the past, we commonly used all parts of natural foods when we consumed a meal. Human eating patterns naturally accessed nutrients available from what was eaten and very little nutrients were wasted as a result. For example, when eating fish, the muscular parts of the fish were consumed along with other parts such as connective tissue. When eating plants, the edible portion of the plant was consumed in its entirety. Our bodies would then filter out what was not consumable, such as the outer shell of a kernel of corn for example. As this occurred, our bodies would extract what nutrients could be found in the food to sustain and grow the human form. This allowed use of local foods to provide nutrients which were available, but was somewhat limited in that foods not available locally could not be used in most cases. Over time, we learned to travel and to ship food from where it was produced to where it could be consumed. Additionally, we learned to prepare foods, removing portions of the food which were either inedible, or undesirable. Removing the inedible parts typically provided some benefit, while parts that were simply undesirable sometimes held valuable ingredients.

Common white kidney beans (*Phaseolus vulgaris*) are frequently available in various foods, but are not commonly consumed regularly by most people. White kidney beans in various prepared form potentially lose nutrients or are combined with foods which counteract nutrients available from the white kidney bean. [weight loss]

Capsicum extract of the fruit of the *Capsicum frutescens* strain originates in the Americas as a pepper, but is generally available worldwide. It is typically used primarily to add spice or spicy heat to dishes. It is generally not recognized as a source of nutrients other than Vitamin B6, or for other health benefits.

Cinnamon extract of the bark of the *Cinnamonium cassia* strain is considered to originate in China, and to be generally available as a seasoning spice. It is generally not considered to be a source of significant nutrients. It generally finds purpose in cooking as a seasoning, used sparingly, and unlikely to provide significant nutrients in most prepare foods as a result.

SUMMARY OF THE INVENTION

A nutritional supplement composition is provided including an extract derived from common white kidney beans (*Phaseolus vulgaris*), Capsicum extract of the fruit of the *Capsicum frutescens* strain and Cinnamon extract of the bark of the *Cinnamonium cassia* strain. The nutritional supplement is in the form of a compound known as CLARIGEST™.

The foregoing, and other features and advantages of various embodiments of the invention, will be apparent from the following, more particular description of the embodiments of the invention, any accompanying drawings, and the claims.

DETAILED DESCRIPTION

A composition is provided as CLARIGEST™. The specific embodiments described in this document represent exemplary instances of the present invention, and are illustrative in nature rather than restrictive.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments.

The composition (referred to as CLARIGEST™) is preferably formed of (1) an extract derived from common white kidney beans (*Phaseolus vulgaris*), (2) capsicum extract of the fruit of the *capsicum frutescens* strain and (3) cinnamon extract of the bark of the *Cinnamonium cassia* strain.

The composition involves taking nutrients from white kidney bean. The common white bean (*Phaseolus vulgaris*) produces an alpha-amylase inhibitor, which has been characterized and tested in numerous clinical studies. Since the alpha-amylase inhibitor is typically not available to consumers in many other circumstances, this provides nutrients potentially vital to cause weight loss. The health benefits of such weight loss cannot be underestimated, and are potentially provided by the extract from the *Phaseolus vulgaris* strain.

The composition further involves retrieving nutrients from capsicum extract of the fruit of the *Capsicum frutescens* strain. This strain is known for including capsaicin. Additionally, while the *Capsicum frutescens* strain is not know for nutrients, it does include substantial amounts of Vitamin C and some Vitamin B6 content as well.

The composition also involves accessing nutrients from Cinnamon extract of the bark of the *Cinnamonium cassia* strain. Cinnamon extract of the *Cinnamonium cassia* strain has been shown to include a rich source of Calcium, iron and Vitamin K. There exists some inconclusive evidence that Cinnamon extract of the *Cinnamonium cassia* strain may also counteract the effects of diabetes. Additionally, compounds in the extract potentially have antioxidant effects.

The composition includes a combination of the three extracts subjected to mixing and binding processes to further link the material provided therein. Typically, the combination of the extracts provides for a mix of potential weight loss and glucose reduction effects. The combination further provides specific materials having potential to aid in providing relief from various other human conditions.

Beyond other effects of the cinnamon extract of the *Cinnamonium cassia* strain, coumarin is also known to often be present in samples of the *Cinnamonium cassia* strain. Coumarin provides a blood thinning effect in some individuals, potentially benefitting individuals suffering from clots, for example. Coumarin is often provided in small doses in Clarigent, to provide for a beneficial effect while not rising to a level which threatens people potentially sensitive to blood thinners.

Additionally, presence of capsaicin in the capsicum extract of the fruit of the *Capsicum frutescens* strain potentially provides for a variety of benefits. For example, capsaicin often acts to help drain sinus cavities and potentially to reduce inflammation of sinus passages as a further benefit.

Moreover, capsaicin potentially provides for other reductions in inflammation in a similar way.

Weight Loss Effects

The common white bean (*Phaseolus vulgaris*) produces an alpha-amylase inhibitor which can assist in weight loss. This alpha-amylase inhibitor is generally present in sufficient quantities to provide weight loss effects by allowing the body to better metabolize and reduce storage of fat. Thus, the extract of the *Phaseolus vulgaris* strain provides a benefit which can allow for improved health and well-being in those consuming it.

Glucose Reduction

The *Phaseolus vulgaris* strain has shown some glucose reduction effects which can assist in reducing the effects of diabetes. Such activity can depend on individual factors. Additionally, the cinnamon extract of the *Cinnamonium cassia* strain has also been shown to potentially have some glucose reduction effects. These materials operate as part of the CLARIGEST™ composition and thereby provide further benefits in those who struggle with glucose.

Additional Beneficial Effects

Beyond the effects specific to the glucose reduction and weight loss activity of the compound, other beneficial effects typically manifest. Reduction of inflammation resulting from presence of the capsaicin in the capsicum extract of the fruit of the *Capsicum frutescens* strain can provide a variety of benefits. Moreover, the ingredients in combination can potentially provide for improved digestion and related improvements resulting from the combination of weight loss effect, glucose moderating and reduced inflammation.

The benefit of the composition includes restoring and enhancing cells. Our cells constantly deteriorate in daily life. If there is no support to restore the deterioration, cellular damage will affect the body functions. CLARIGEST™ composition is a supplementary factor that can restore the cells to the body balance without drug and substance usage. When cells are restored, in the next process, CLARIGEST™ composition may accordingly boost cell strength, equivalent to increasing the effectiveness and the number of cells, while maximizing physical and mental abilities After the cellular restoration and boosting the cell strength, the next challenge is the protection to maintain the long-lasting quality of the cells. CLARIGEST™ dietary supplement may help to protect and delay the cellular deterioration. This will also result in improving the immune system, as the immune system no longer needs to activate against inflammation or other forms of deterioration. When the cell functions are systematically restored, boosted and protected, CLARIGEST™ dietary supplement may directly enhance physical and mental capacity to go beyond limits at each age and to live life fully as the pace of life requires a strong response to maintain youth and vigor.

The health benefits of CLARIGEST™ are also potentially of value to children, and help to develop the strength of new cells and protect cells from early deterioration. Both are beneficial to the development of body, intelligence, memory, and positive emotions. The physical results may include i) reduce waste of nutrients in fat cells, ii) restore cells for normal growth in each stage, iii) recover from illness, iv) build muscle, v) boost the immune system, vi) reduce the risk of the incidence of disease, vii) promote growth to maximum effectiveness, viii) adjust height, ix) improve body growth, x) efficient immunity and xi) increase energy. The weight loss and inflammation reduction properties are potentially of particular assistance to children, as the effects allow for better childhood development and less likelihood of obesity later in life.

The composition also helps to restore the old damaged cells, repair damaged body tissues, delay the cellular deterioration, inhibit free radicals, and help the process of skin cell renewal in adults for glowing skin and younger appearance. Reducing weight and moderating glucose as previously mentioned contribute to enhancing balance, reducing exhaustion from stress and demands of healing, improving concentration and work efficiency, and boosting the immune system to stay healthy.

Physical results may also include: a radiant and vibrant skin, younger appearance; reducing fatigue at work; restoring the reproductive system; refreshing the body; boosting the immune system; protecting against free radical formation; and preventing premature aging.

The compounds are typically dried and ground or milled to small particles, and subsequently combined in the desired ratio. The combination may remain as a powder to be added to food or pressed in a tablet. Alternatively, the compounds may be mixed in an aqueous or other liquid solution and thereby provided in liquid form.

In an embodiment, a preferred dosage, the total compound blended is 155 mg, pressed into a single tablet, potentially with additional inactive ingredients to allow for consumption and ease of use. The compound may be sold under the CLARIGEST™ name. The dosage may include a combination of 100 mg of white kidney bean extract of the *Phaseolus vulgaris* strain, 30 mg of cinnamon extract of the bark of the *Cinnamonum cassia* strain , and 25 mg of the capsicum extract of the fruit of the *Capsicum frutescens* strain. In other embodiments, other ratios of the ingredients may be provided, and smaller or larger dosages may be used for particular applications. Variations may be provided to increase specific benefits such as weight loss or inflammation reduction, for example.

Study of CLARIGEST™ Effectiveness

A study of users of a trial formulation was conducted. The study focused in part on appetite control, weight-loss and nutritional factors, but also considered other possible results. Participants reported the following results:

Ninety percent (90%) of participants reported reduced intestinal fat absorption, with a response of up to ninety percent (90%) decrease in intestinal fat absorption as a measured result.

Eighty percent (80%) of participants reported increased basal metabolic rates, with a typical measured result of thirty percent (30%) greater basal metabolic rate.

Ninety percent (90%) of participants reported better burning of stubborn fat found in the abdomen and thigh in exercise and weight-loss activity. The participants reported a measured result of sixty-five percent (65%) reduction in so-called stubborn fat.

Eighty-three percent (83%) of participants reported increases in a partial ketosis state. The participants reported entrance into the partial ketosis state in an effective and comfortable manner with use of CLARIGEST™.

Ninety-five percent (95%) of participants also reported decreases in undesirable aspects of ketosis states such as low energy, "ketoflu" or micronutrient deficiencies.

Eighty-seven percent (87%) of participants reported increased sensations of dermal tightening even in weight loss and diet control activities, with a typical measured result of an eighty percent (80%) tightening.

Ninety-two percent (92%) of participants were found to have a reduction in weight regain after weight loss, showing as much as eighty percent (80%) less weight regain.

Eighty-three percent (83%) of participants reported better micro bacterial environment in intestines. The participants reported a ninety percent (90%) improvement in micro bacterial environment in the intestines compared to indications prior to use of CLARIGEST™.

Eighty-two percent (82%) of participants reported reported increased brain function, typically reporting a seventy percent (70%) increase in speed of brain function during use of CLARIGEST™ despite diet control aspects of weight loss regimens.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claim.

What is claimed is:

1. A tablet consisting essentially of a *phaseolus vulgaris* extract, an extract of the fruit of *capsicum frutescens*, and a bark extract of *cinnamonium cassia.*

2. The tablet of claim 1, wherein the *phaseolus vulgaris* extract is present at 100 mg, the extract of the fruit of *capsicum frutescens* is present at 25 mg and the bark extract of *cinnamonium cassia* is present at 30 mg.

* * * * *